United States Patent [19]

Zoll et al.

[11] Patent Number: 5,848,090
[45] Date of Patent: *Dec. 8, 1998

[54] ADJUSTED LASER CAVITY RESONATOR AND METHOD FOR PREPARING A LASER RESONATOR

[75] Inventors: Martin Zoll, Gechingen; Martin Wunderling, Herrenberg, both of Germany

[73] Assignee: Hewlett-Packard Company, Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 668,557

[22] Filed: Jun. 21, 1996

[30] Foreign Application Priority Data

Jul. 21, 1995 [EP] European Pat. Off. ............... 95111484

[51] Int. Cl.[6] ..................................................... H01S 3/081
[52] U.S. Cl. .............................. 372/93; 372/64; 372/97; 372/107
[58] Field of Search .............................. 372/94, 107, 64, 372/92, 97, 61, 93

[56] References Cited

U.S. PATENT DOCUMENTS

| | | | |
|---|---|---|---|
| 3,970,963 | 7/1976 | Chester | 372/64 |
| 4,271,397 | 6/1981 | Stiles et al. | 372/94 |
| 4,387,344 | 6/1983 | Meyer | 372/94 |
| 4,438,514 | 3/1984 | Chenausky et al. | 372/64 |
| 4,628,515 | 12/1986 | Rodloff et al. | 372/94 |
| 4,972,428 | 11/1990 | Hinz et al. | 372/107 |
| 5,020,074 | 5/1991 | Lerfald | 372/107 |
| 5,048,046 | 9/1991 | Welsch et al. | 372/61 |
| 5,054,032 | 10/1991 | Krueger et al. | 372/61 |
| 5,088,824 | 2/1992 | Killpatrick et al. | 372/94 |
| 5,373,360 | 12/1994 | Martin et al. | 372/108 |
| 5,426,662 | 6/1995 | Mefferd et al. | 372/99 |
| 5,432,610 | 7/1995 | King et al. | |

Primary Examiner—Leon Scott, Jr.

[57] ABSTRACT

Method for preparing a laser cavity resonator for use in a Raman gas analyzer, that resonator comprises a V-shaped housing which comprises a first and a second channel for the laser beam in a V-arrangement. The method allows the adjustment of the resonator in the manufacturing site and provides a high mechanical stability and reliability of the system and accelerates the manufacturing of the resonator. The resonator received by the method comprises adjusted mirrors fixed to the housing so that the resonator can be transported and installed in the analysis system at its place of application.

12 Claims, 2 Drawing Sheets

ADJUSTED LASER CAVITY RESONATOR AND METHOD FOR PREPARING A LASER RESONATOR

FIELD OF THE INVENTION

The invention relates to a method for preparing a laser cavity resonator for use in a gas analyzer. Further, the invention relates to an adjusted laser cavity resonator which is provided by this method.

BACKGROUND OF THE INVENTION

The monitoring of respiratory gases in the operating room is increasingly important in improving patient safety during anesthesia. Thus, Raman light scattering has been successfully used in critical care situations to continuously monitor these gases. This technic is based on the effect which occurs when monochromatic light interacts with vibrational/rotational modes of gas molecules to produce scattered light which is frequency shifted from that of the incident radiation by an amount corresponding to the vibrational/rotational energies of the scattering gas molecules. A further description can be found in U.S. Pat. No. 5,153,671.

Systems developed for analysis of gases in critical care situations utilizing Raman scattering typically employ gas cells which contain a sample of the patients respiratory gas to be analyzed. The gas sampling cell is located either within the resonant cavity of a laser or outside the cavity. In an intra cavity system, a laser beam is directed through the resonant cavity such that it intercepts the gas within the sampling cell. Raman scattered light from the gas analysis region within the cell is collected by a collection optic and directed through a spectrograph or interference filters. The collection optics and interference filters or spectrograph and possibly focusing optics in turn transmit the Raman scattered light to appropriate detectors or detector array for quantifying each specific Raman signal, and thus, each specific gas comprising the respiratory sample.

The co-pending European Patent Application 95 302 412.2 filed on Apr. 11, 1995 by the applicant with the title "A Diode-Pumped Power Build-Up Cavity for Chemical Sensing" describes a laser Raman gas analysis system using low cost and low power diode lasers. In this system light from a diode laser is coupled into a build-up cavity so that the power of the intra cavity light is much larger than the power of the incident light. This is facilitated by ensuring that the build-up cavity is impedance-matched to the incident light beam, and that a portion of the intra cavity light is coupled back into the diode laser. A gas sample is introduced into the build-up cavity, and the optical signal generated by the interaction of the intra cavity light and gas sample can be measured. The build-up cavity used in this gas analysis system comprises a V-shaped housing which comprises a first and a second channel for the laser beam in a V-arrangement and reflector mirrors for each beam and an input/output coupler mirror at the intersection point of the two channels. The V-shaped cavity generates an intra cavity beam in the second channel which also passes through a sample in the first channel being in line with the light source and the optical arrangements. The optical signal generated by the interaction of the beam with the sample is detected by a detection system. A small portion of the beam leaves through the input/output coupler mirror and passes through the optical arrangement into the diode laser. This provides measurement advantages of this system.

Generally, for manufacturing such a laser cavity resonator it is a time-consuming process to adjust the mirrors in such a housing so that the system can easily be assembled at the place of application. Further, it is necessary to make sure that for example during the transport the adjusted mirrors are not shifted.

Thus, the invention as claimed is intended to remedy this drawbacks. It solves the problem of providing a method for preparing a laser cavity resonator which allows a safe and fast adjustment of the mirrors and further it solves the problem of providing a stable adjusted laser cavity resonator.

SUMMARY OF THE INVENTION

According to the present invention the method for preparing a laser cavity resonator with a V-shaped housing, as described above, generally comprises the following steps:

1. Providing a housing ready to receive the reflector mirrors in front of the first and second channel openings and the input/output coupler mirror at the intersection point of the longitudinal axis of the first and second channels;
2. providing mirror holders in which the mirrors are fixed, said mirror holders are adapted to be fixed to said housing in front of said respective openings;
3. mounting of said housing relative to an auxiliary laser;
4. adjusting said reflector mirrors to said auxiliary laser beam and fixing said mirrors in their position;
5. adjusting said input/output coupler mirror to a second laser beam supplied by a laser diode arranged in the longitudinal axis of at least one of said channels for obtaining maximum resonator intensity, and fixing to said housing.

The V-shaped housing is either constructed as one block or with a bottom member and a top member that can be manufactured by alumina die casting which allows production of an exact cavity at low cost. The surface can be coated with a thin layer of nickel to prevent corrosion of the housing. The reference areas, especially the front sides in the regions of the free end of the channels to which the holder of the reflector mirrors will be fixed, can be finished in order to provide the required tolerances dependent on the adjustment principle. The openings in the housing serve to attach the mirrors in front of the openings to reflect the light back into the respective channel. Thus, dependent on the construction of the mirror holder, the reflector mirrors can be fixed at the housing at the front sides or in special recesses which are in line with the longitudinal axes of the first and second channels and which have preferably a circular circumference. The latter allows the usually circular mirrors to be moved within the opening in perpendicular directions to the longitudinal axis of the channel and the cylindrical opening.

The mirror holder to which each reflector mirror is fixed comprises a plate like member which comes into contact with the front side of the housing. The mirror holder can be held in this position by suction means and moved by a XYZ-table in each direction. This can be accomplished by either fastening the mirror holder to the XYZ-table by vacuum suction or by fastening the mirror holder to the housing by vacuum suction and displacement of the holder by engaging means attached to the XYZ-table. In case of a two member housing, the housing is longitudinally divided into a bottom member and a top member, so that the optical part like circular openings and circular channels are divided in the middle. Thus, the recesses in the housings form troughs in which the mirror holders can be inserted for adjusting the resonator. After adjustment the cavity is closed by fixing the top member to the bottom member with appropriate means, for example screws.

The mirrors used for the reflector mirrors are concave or concentrating mirrors and the mirror used as input/output coupler mirror can be a concave mirror or a plane mirror. The reflector mirrors are fixed to their respective holder, for example by an adhesive.

To enable adjustment, the housing is mounted to a holder which is mechanically connected and aligned to an auxiliary laser. The holder has a fixed point relative to the laser which serves as reference for the housing. The adjustment of the housing, which is necessary because of manufacturing tolerances, and the reflector mirrors, is performed by use of an auxiliary laser beam. For this, the first reflector mirror is attached in front of the respective opening and aligned to the auxiliary laser beam by lateral and/or perpendicular movement and/or tilt to the longitudinal axis of the first channel until the laser beam is reflected in its longitudinal axis. This can be accomplished by an XYZ-table or other appropriate means. Subsequently the mirror is fixed to the housing, preferably by an adhesive. The adjustment of the second reflector mirror is performed in similar manner. For this, the housing is put in a second position which allows the auxiliary laser beam to be aligned to the second channel and to adjust the second reflector mirror. The second reflector mirror is not finally fixed to the housing in order to allow a precision adjustment for obtaining maximum resonator intensity after having adjusted the input/output coupler mirror.

After the adjustment of the reflector mirrors the auxiliary laser beam is switched off and a second laser beam supplied by a laser diode which also is mechanically connected and aligned to a fix point of the holder is directed to the second channel.

After placement of the input/output coupler mirror in front of the respective opening the mirror is adjusted. A preadjustment of the input/output coupler mirror can be accomplished by directing a laser beam produced by the auxiliary laser or the laser diode on the mirror until the reflected part impinges on the respective other laser (laser diode or auxiliary laser). If the resonator has already started to amplify, the mirror holder is secured in its position at the housing by an adhesive. Finally, a precision adjustment of the resonator intensity can be performed by minor displacement of the second reflector mirror. Subsequently, the mirror holder of the second reflector mirror is fixed to the housing.

This method allows the preparation of an adjusted laser cavity resonator at the manufacturing site by use of the usual optical means like optical bank, auxiliary laser and further standard optical means. Thus, the expensive parts for adjusting the resonator can remain in the laboratory and the resonator easily can be installed at its application place. The present method provides a laser cavity resonator which can be manufactured with low cost components by high mechanical stability and functional reliability of the system. The method allows a reduced production time and the automatic manufacturing. Further, the assembly can be serviced easily.

The method for preparing the adjusted laser cavity resonator provides a special resonator housing having the advantages as mentioned above.

BRIEF DESCRIPTION OF THE DRAWINGS

These and other advantages and objects of the present invention can be taken from the following description of preferred embodiments in accordance with the accompanying drawings, in which.

DETAILED DESCRIPTION OF THE PREFERRED EMBODIMENT

Figure 1:
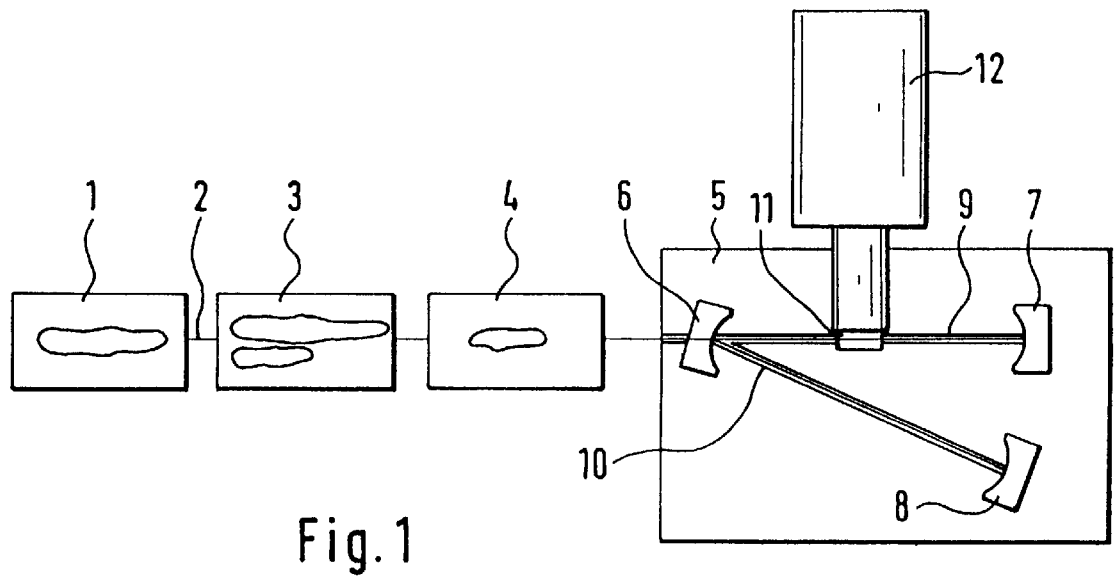
FIG. 1 is a schematic view of the Raman gas analysis system.

FIG. 1 shows schematically the gas analysis system with the light source 1 which is a diode laser. The light beam 2 passes through optical means 3 for forming the laser beams and subsequent through optical filter 4 which are known to subsequently a person skilled in the art. The light beam 2 impinges on a cavity 5 which comprises an input/output coupler mirror 6 and reflector mirrors 7 and 8. The cavity 5 further comprises a first channel 9 and a second channel 10 for the laser beam. The laser beam in the first channel 9 passes through a sample 11 and the optical signal generated by the interaction of the laser beam with sample 11 is detected by detection system 12, which is a spectrometer. A small portion of the laser beam leaks through mirror 6 along a line exactly on top of the beam generated by the light source 1 but in the opposite direction and passes through the optical filter 4 and the optical means 3 into the diode laser 1. Further details concerning the system can be found in the above mentioned co-pending European Patent Application 95 302 412.2 filed on Apr. 11, 1995 by the applicant.

Figure 2:
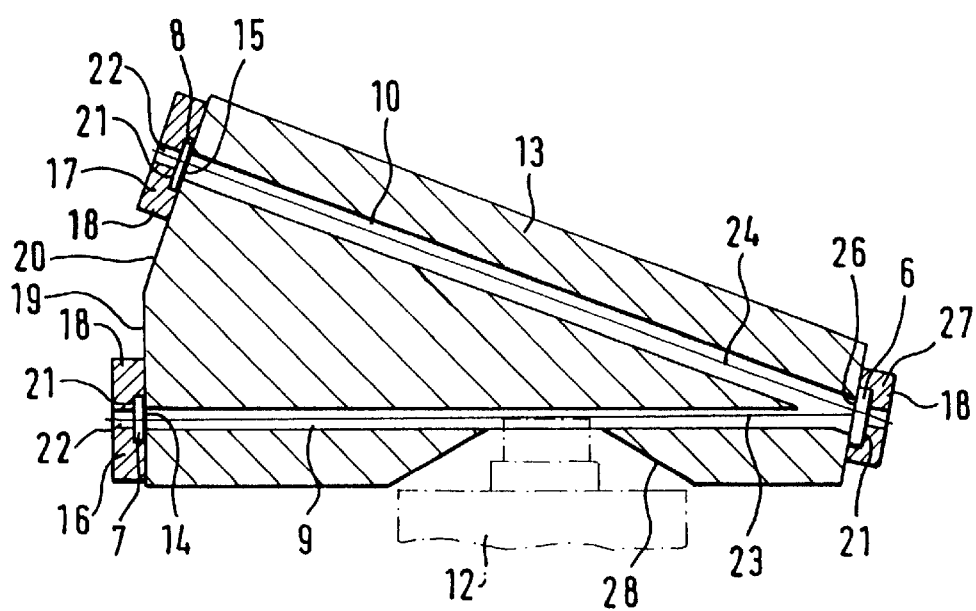
FIG. 2 shows a cross sectional view through the housing and a top view of the housing.

FIG. 2 shows the housing 13 of the laser resonator cavity. The housing is V-shaped and comprises openings 14 and 15 in front of which the first reflector mirror 7 and the second reflector mirror 8, respectively, are arranged in line with the longitudinal axis of the respective first channel 9 and second channel 10. The mirrors 6, 7, 8 are held in front of the openings 14, 15, 26, respectively, by respective mirror holders 16, 17, 27. The mirror holders 16, 17, 27 comprise a plate like member 18 which is attached to the respective front side 19 and 20. The diameter of the plate like member is larger than the diameter of the respective openings. In this embodiment the mirror holders 16, 17, 27 further comprise a recess 21 to receive the respective mirror 6, 7, and 8. At least the mirror holders 16, 17 further comprise a boring 22 which is used to control the intensity of the resonator during the adjustment process. The mirror holders are held by vacuum suction to an XYZ-table as shown in FIG. 4. The mirrors 6, 7, 8 are fixed to the mirror holders 16, 17, 27 by an adhesive.

The opening 26 in front which the input/output coupler mirror 6 is arranged, is at the intersection point of the longitudinal axis 23 of the first channel and the longitudinal axis 24 of the second channel. The housing further comprises a recess 28 for coupling a light pipe of the detection system 12. The sample is inserted in the first channel 9.

Figure 3:
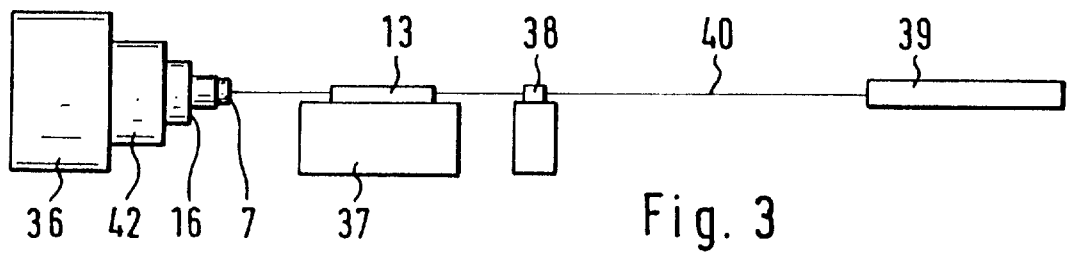
FIG. 3 shows the lateral view of the adjustment arrangement.

FIG. 3 shows a schematic side view of the adjustment arrangement with the XYZ-table 36, a mirror holder 16 with a reflector mirror 7. The V-shaped housing 13 is placed on a appropriate holder 37, a laser diode 38 and the HeNe auxiliary laser 39 providing a laser beam 40. XYZ-table 36 together with the mirror holder 16 and the reflector mirror 7 are depicted exploded from the housing 13.

Figure 4A:
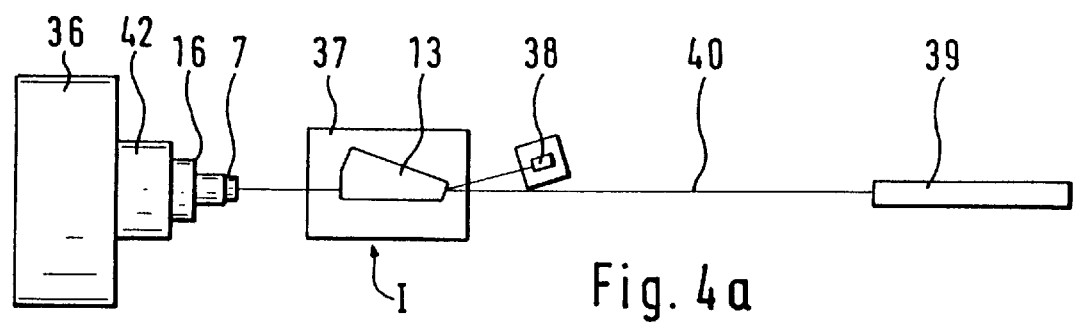
FIGS. 4a and 4b shows the top view of the adjustment arrangement with the cavity in different positions.
Figure 4B:
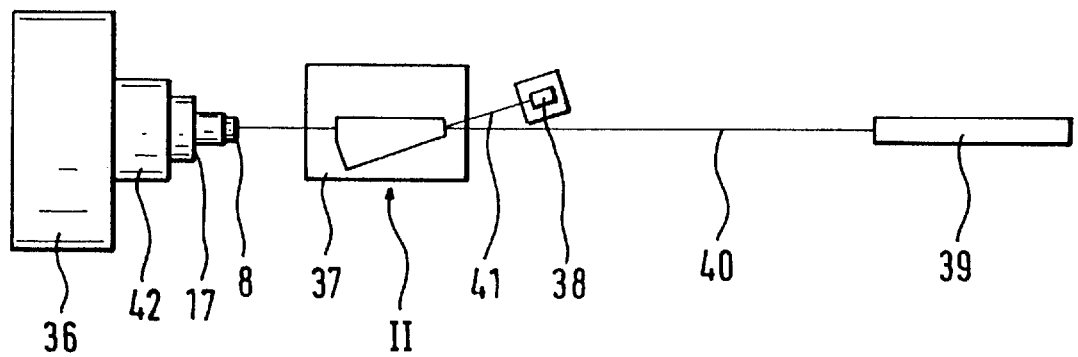

The adjustment process for the laser cavity resonator is now explained in general in connection with FIGS. 4a and 4b showing the housing 13 in a first adjustment position I (FIG. 4a) and a second adjustment position II (FIG. 4b). According to the preferred embodiment the method comprises:

Mounting the housing 13 to the holder 37 which is mechanically connected and aligned to the auxiliary laser 39 and the laser diode 38, for example in view of a fix point; aligning of the first channel 9 to the auxiliary laser beam 40 of said auxiliary laser 39 by placing the housing 13 in a fist position I, holding of the first mirror holder 16 in front of the opening 14 of the first channel 9; displacement of the mirror holder 16 by the XYZ-table 36 in each necessary direction until the laser beam is reflected in its longitudinal axis, and fixing the mirror holder 16 to the housing 13; aligning of the second channel 10 by placing the housing 13 in a second position II so that the second channel and the auxiliary laser 39 are in line; holding of the second mirror holder 8 in front of the opening 15 of the second channel 10; displacement of the mirror holder 17 by the XYZ-table 36 until the laser beam is reflected in its longitudinal axis; switching off of the auxiliary laser 39 and aligning a laser beam 41 of a laser diode 38 to the first channel 9 in the second position II of the housing 13; arrangement of the input/output coupler mirror holder 27 in front of the respective opening 26 for obtaining maximum resonator intensity and fixing the input/output mirror holder by an adhesive to the housing; and controlling and precision adjustment of the second reflector mirror 8 for obtaining maximum resonator intensity and fixing the mirror holder 17 to the housing 13.

The adjustment of the input/output coupler mirror and the precision adjustment of the second reflector mirror 8 for obtaining maximum resonator intensity is performed by determining the transmission losses which are 12 ppm. The part of the laser beam which passes through the mirror passes through the boring 22 (FIG. 2) and is detected by appropriate instruments known to a person skilled in the art.

The change of the housing from the first position I to the second position II is performed by use of an alignment pin (not shown) which allows a continuous and fast adjustment of the exactly and identically manufactured housings of the resonators for different Raman gas analysis systems.

We claim:

1. Method for preparing a laser cavity resonator, said resonator comprising a V-shaped housing for laser beams including a first channel and a second channel and openings for reflector mirrors for each beam and an opening for an input/output coupler mirror, said method comprising:
   a) providing a housing ready to receive the reflector mirrors in front of openings to the first channel and second channel and the input/output coupler mirror, at an intersection point of longitudinal axes of the first channel and the second channel;
   b) providing mirror holders in which the reflector mirrors are fixed, said mirror holders configured to be fixed to said housing in front of said openings;
   c) mounting said housing in a beam path of an auxiliary laser;
   d) adjusting said reflector mirror holders with respect to a beam from said auxiliary laser and fixing said mirror holders in their position;
   e) adjusting said input/output coupler mirror with respect to a second laser beam supplied by a laser diode arranged in the longitudinal axis of at least one of said channels, so as to obtain maximum resonator intensity, and fixing said input/output coupler mirror to said housing.

2. Method of claim 1, wherein step b) further comprises:
concentrically aligning each said mirror holder to the beam of said auxiliary laser; and
aligning each reflector mirror associated with each mirror holder relative to the longitudinal axis of said associated holder so that said laser beam is reflected back along its longitudinal axis.

3. Method of claim 1, wherein step d) further comprises:
holding said first reflector mirror in front of the opening of said first channel, aligning said first reflector mirror to said auxiliary laser beam by perpendicular or tilting movement relative to the longitudinal axis of said first channel until said laser beam is reflected along its longitudinal axis, and fixing said first reflector mirror to the housing; and
holding said second reflector mirror in front of the opening of said second channel, aligning said second reflector mirror to said auxiliary laser beam by perpendicular or tilting movement relative to the longitudinal axis of said second channel until said laser beam is reflected along its longitudinal axis.

4. Method of claim 1, wherein step e) further comprises:
placing said input/output coupler mirror in front of said opening, axially and laterally moving said input/output coupler mirror to obtain maximum resonator intensity, and then fixing said mirror with its holder in position.

5. Method of claim 1, comprising:
mounting said housing to a holder which is mechanically connected and aligned to said auxiliary laser and said second laser;
aligning of the first channel with the auxiliary laser beam of said auxiliary laser by placing said housing in a first position so that said first channel and said auxiliary laser beam are in line;
holding said first mirror holder in front of said opening of said first channel, displacing said mirror holder until said laser beam is reflected along its longitudinal axis, and fixing said mirror holder to the housing;
aligning said second channel by placing said housing in a second position so that said second channel and said auxiliary laser beam are in line;
holding of second mirror holder in front of said opening of said second channel, displacing said mirror holder until said laser beam is reflected along its longitudinal axis;
switching off said auxiliary laser and aligning a laser beam of a laser diode to said first channel in said second position of said housing;
moving said input/output coupler mirror holder in front of said respective opening to obtain maximum resonator intensity and then fixing said holder to the housing; and
adjusting said second reflector mirror to obtain maximum resonator intensity and fixing said mirror holder to the housing.

6. A laser cavity resonator including a channel exhibiting a longitudinal axis and opposed apertures at each end of said channel, said laser cavity resonator further comprising:
a mirror positioned at each of said opposed apertures of said channel, each said mirror including a curved reflective surface for interacting with a laser beam in said channel; and
means for positioning each said mirror in a direction that is perpendicular to said longitudinal axis of said channel so that curved reflective surface of each said mirror is positioned to direct the laser beam along said longitudinal axis.

7. The laser cavity resonator as recited in claim 6, wherein said curved reflective surface of each said mirror is concave.

8. The laser cavity resonator as recited in claim 6, wherein said means for positioning comprises a mirror holder for each said mirror, each said mirror holder being a plate like member with a recess for the mirror and which has a diameter larger than a diameter of an adjoining aperture.

9. The laser cavity resonator as recited in claim 8, wherein said plate like member of said mirror holder is adhered to the housing.

10. A method for configuring a laser cavity resonator which includes a channel exhibiting a longitudinal axis and opposed apertures at each end of said channel, said laser cavity resonator further including a mirror positioned at each of said opposed apertures of said channel, each said mirror including a curved reflective surface, said method comprising the steps of:

a) introducing a laser beam into said channel; and b) adjusting a position of each said mirror in a direction that is perpendicular to said longitudinal axis of said channel so that said curved reflective surface of each said mirror is positioned to reflect the laser beam along said longitudinal axis.

11. The method as recited in claim 6, wherein said curved reflective surface of each said mirror is concave.

12. The method as recited in claim 10, further comprising the step of:

c) adhering each said mirror to the housing subsequent to step b).

* * * * *